(12) United States Patent
Falco et al.

(10) Patent No.: US 6,271,031 B1
(45) Date of Patent: Aug. 7, 2001

(54) QUINOLINATE METABOLISM ENZYMES

(75) Inventors: Savero Carl Falco, Arden; Layo O. Famodu, Newark; J. Antoni Rafalski, Wilmington, all of DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/370,473

(22) Filed: Aug. 9, 1999

Related U.S. Application Data

(60) Provisional application No. 60/096,240, filed on Aug. 12, 1998.

(51) Int. Cl.[7] .............................. C12N 5/02; C12N 9/02; C12N 1/20; C12N 15/70; C07C 51/235

(52) U.S. Cl. .................. 435/410; 435/189; 435/252.33; 435/320.1; 536/23.2

(58) Field of Search .............................. 435/252.33, 189, 435/320.1, 410; 536/23.2

(56) References Cited

PUBLICATIONS

Hosokawa et al, Biochem. Biophys. Res. Commun., (1983), 111, No. 1, 188–193.*
Wilder et al, Biochem. Biophys. Res. Commun., (1984), 123, No. 2, 836–841.*
Eads, J. C. et al., (1997), Structure, 5:47–58.
NCBI General Identifier No. 2498610.
NCBI General Identifier No. 2498608.
NCBI General Identifier No. 4262242.
NCBI General Identifier No. 2499961.
Tedeschi et al., (1987), Biochemistry, 36:16221–16230.

* cited by examiner

*Primary Examiner*—Nashaat T. Nashed
*Assistant Examiner*—Malgorzata A. Walicka

(57) ABSTRACT

This invention relates to an isolated nucleic acid fragment encoding a quinolinate metabolic enzyme. The invention also relates to the construction of a chimeric gene encoding all or a portion of the quinolinate metabolic enzyme, in sense or antisense orientation, wherein expression of the chimeric gene results in production of altered levels of the quinolinate metabolic enzyme in a transformed host cell.

6 Claims, No Drawings

US 6,271,031 B1

QUINOLINATE METABOLISM ENZYMES

This application claims the benefit of U.S. Provisional Application No. 60/096,240, filed Aug. 12, 1998.

FIELD OF THE INVENTION

This invention is in the field of plant molecular biology. More specifically, this invention pertains to nucleic acid fragments encoding enzymes involved in quinolinate metabolism in plants and seeds.

BACKGROUND OF THE INVENTION

The nicotinamide moiety of the nicotinamide coenzymes ($NAD^+$ and $NADP^+$) is derived, in humans, from dietary nicotinamide, nicotinic acid, or the essential amino acids tryptophan or aspartate. Quinolinate is an intermediary in this pathway. L-aspartate oxidase is one of the two components of the quinolinate synthase complex, which is responsible for the conversion of L-asparate and dihydroxyacetone phosphate into quinolinate. L-aspartate oxidase (EC 1.4.3.16) catalyzes the FAD-dependent oxidation of L-aspartate to iminoaspartate, the intermediate that leads to the formation of quinolinate.

Quinolinic acid is a neurotoxin and has been shown to be present at high levels in the central nervous system of patients with certain diseases, such as AIDS, epilepsy, and meningitis. The enzyme quinolinic acid phosphoribosyltransferase provides the only route for quinolinic acid metabolism and is also an essential step in de novo NAD biosynthesis. Quinolinic acid phosphoribosyltransferase (EC 2.4.2.19) is referred to as nicotinate-nucleotide phosphorylase (carboxylating), or quinolinate phosphoribosyltransferase (decarboxylating). This enzyme catalyzes the synthesis of nicotinic acid mononucleotide from quinolinic acid and 5-phosphoribosyl-1-pyrophosphate. The seven-stranded alpha/beta-barrel domain of quinolinic acid phosphoribosyltransferase is very similar in structure to the eight-stranded alpha/beta-barrel enzymes. The structure shows a phosphate-binding site that appears to be conserved among many alpha/beta-barrel enzymes including indole-3-glycerol phosphate synthase and flavocytochrome b2 (Eads, J. C. et al. (1997) *Structure* 5:47–58). Nicotinate-nucleotide phosphorylase from human liver and brain has been cloned, sequenced and analyzed (Okuno, E. et al. (1988) *J. Biochem.* (Tokyo) 103:1054–1059.).

Nicotinate-nucleotide phosphorylase and L-aspartate oxidase have been widely studied in prokaryotes and in mammals but they have not yet been described in plants.

SUMMARY OF THE INVENTION

The instant invention relates to isolated nucleic acid fragments encoding quinolinate metabolic enzymes. Specifically, this invention concerns an isolated nucleic acid fragment encoding an L-aspartate oxidase or a nicotinate-nucleotide pyrophosphorylase and an isolated nucleic acid fragment that is substantially similar to an isolated nucleic acid fragment encoding an L-aspartate oxidase or a nicotinate-nucleotide pyrophosphorylase. In addition, this invention relates to a nucleic acid fragment that is complementary to the nucleic acid fragment encoding L-aspartate oxidase or nicotinate-nucleotide pyrophosphorylase.

An additional embodiment of the instant invention pertains to a polypeptide encoding all or a substantial portion of a quinolinate metabolic enzyme selected from the group consisting of L-aspartate oxidase and nicotinate-nucleotide pyrophosphorylase.

In another embodiment, the instant invention relates to a chimeric gene encoding an L-aspartate oxidase or a nicotinate-nucleotide pyrophosphorylase, or to a chimeric gene that comprises a nucleic acid fragment that is complementary to a nucleic acid fragment encoding an L-aspartate oxidase or a nicotinate-nucleotide pyrophosphorylase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding an L-aspartate oxidase or a nicotinate-nucleotide pyrophosphorylase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of an L-aspartate oxidase or a nicotinate-nucleotide pyrophosphorylase in a transformed host cell comprising: a) transforming a host cell with a chimeric gene comprising a nucleic acid fragment encoding an L-aspartate oxidase or a nicotinate-nucleotide pyrophosphorylase; and b) growing the transformed host cell under conditions that are suitable for expression of the chimeric gene wherein expression of the chimeric gene results in production of altered levels of L-aspartate oxidase or nicotinate-nucleotide pyrophosphorylase in the transformed host cell.

An addition embodiment of the instant invention concerns a method for obtaining a nucleic acid fragment encoding all or a substantial portion of an amino acid sequence encoding an L-aspartate oxidase or a nicotinate-nucleotide pyrophosphorylase.

A further embodiment of the instant invention is a method for evaluating at least one compound for its ability to inhibit the activity of an L-aspartate oxidase or a nicotinate-nucleotide pyrophosphorylase, the method comprising the steps of: (a) transforming a host cell with a chimeric gene comprising a nucleic acid fragment encoding an L-aspartate oxidase or a nicotinate-nucleotide pyrophosphorylase, operably linked to suitable regulatory sequences; (b) growing the transformed host cell under conditions that are suitable for expression of the chimeric gene wherein expression of the chimeric gene results in production of L-aspartate oxidase or nicotinate-nucleotide pyrophosphorylase in the transformed host cell; (c) optionally purifying the L-aspartate oxidase or the nicotinate-nucleotide pyrophosphorylase expressed by the transformed host cell; (d) treating the L-aspartate oxidase or the nicotinate-nucleotide pyrophosphorylase with a compound to be tested; and (e) comparing the activity of the L-aspartate oxidase or the nicotinate-nucleotide pyrophosphorylase that has been treated with a test compound to the activity of an untreated L-aspartate oxidase or nicotinate-nucleotide pyrophosphorylase, thereby selecting compounds with potential for inhibitory activity.

BRIEF DESCRIPTION OF THE SEQUENCE LISTING

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Quinolinate Metabolic Enzymes

|  |  | SEQ ID NO: | |
| --- | --- | --- | --- |
| Protein | Clone Designation | (Nucleotide) | (Amino Acid) |
| Corn L-Aspartate Oxidase | p0118.chsay63r | 1 | 2 |
| Soybean L-Aspartate Oxidase | sr1.pk0068.c11 | 3 | 4 |
| Wheat L-Aspartate Oxidase | wr1.pk0026.e3:fis | 5 | 6 |
| Tobacco Nicotinate-Nucleotide Pyrophosphorylase | tdr1c.pk002.j10 | 7 | 8 |
| Wheat Nicotinate-Nucleotide Pyrophosphorylase | w1m96.pk036.o11 | 9 | 10 |
| Wheat Nicotinate-Nucleotide Pyrophosphorylase | wr1.pk0104.h5 | 11 | 12 |

The Sequence Listing contains the one letter code for nucleotide sequence characters and the three letter codes for amino acids as defmed in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases results in substitution of one or more amino acids, but do not affect the finctional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed MRNA upstream of the translation start sequence. The translation leader sequence may affect processing of the primary transcript to MRNA, MRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting MRNA processing or gene expression. The polyadenylation signal is usually characterized by affecting the addition of polyadenylic acid tracts to the 3' end of the MRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or MRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (MRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of MRNA; i.e., with pre- and propeptides still present. Pre- and propeptides may be but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several quinolinate metabolic enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other L-aspartate oxidases or nicotinate-nucleotide pyrophosphorylases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the MRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of NAD synthesis and/or tryptophan usage in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of MRNA expression, Western analysis of protein expression, or phenotypic analysis.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded quinolinate metabolic enzyme. An example of a vector for high level expression of the instant polypeptides in a bacterial host is provided (Example 7).

Additionally, the instant polypeptides can be used as targets to facilitate design and/or identification of inhibitors of those enzymes that may be useful as herbicides. This is desirable because the polypeptides described herein catalyze various steps in quinolinate metabolism. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, soybean, tobacco and wheat tissues were prepared. The characteristics of the libraries are described below.

TABLE 2 cDNA Libraries from Corn, Soybean, Tobacco and Wheat

| Library | Tissue | Clone |
|---------|--------|-------|
| p0118 | Corn Stem Tissue Pooled From the 4th and 5th Internodes Subtending The Tassel At Stages V8–V12*, Night Harvested** | p0118.chsay63r |
| sr1 | Soybean Root | sr1.pk0068.c11 |
| tdr1c | Nicotiana Benthamiana Developing Root | tdr1c.pk002.j10 |
| wlm96 | Wheat Seedlings 96 Hours After Inoculation With *Erysiphe graminis* f. sp tritici | w1m96.pk036.o11 |
| wr1 | Wheat Root From 7 Day Old Seedling | wr1.pk0026.e3 |
| | | wr1.pk0104.h5 |

*Corn developmental stages are explained in the publication "How a corn plant develops" from the Iowa State University Coop. Ext. Service Special Report No. 48 reprinted June 1993.
**This library was normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding quinolinate metabolic enzymes were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding L-Aspartate Oxidase

The BLASTX search using the EST sequences from clones listed in Table 3 revealed similarity of the polypeptides encoded by the cDNAs to L-aspartate oxidase from Synechocystis sp. *Pseudomonas aeruginosa* (NCBI General Identifier Nos. 2498610 and 2498608, respectively). Shown in Table 3 are the BLAST results for individual ESTs ("EST"), or the sequences of the entire cDNA inserts comprising the indicated cDNA clones ("FIS"):

TABLE 3

BLAST Results for Sequences Encoding Polypeptides Homologous to L-Aspartate Oxidase

| Clone | Status | NCBI General Identifier No. | BLAST pLog Score |
|-------|--------|----------------------------|------------------|
| p0118.chsay63r | EST | 2498610 | 25.52 |
| sr1.pk0068.c11 | EST | 2498608 | 8.52 |
| wr1.pk0026.e3 | FIS | 2498608 | 84.22 |

The data in Table 4 represents a calculation of the percent identity of the amino acid sequences set forth in SEQ ID NOs:2, 4 and 6 and the Synechocystis sp. *Pseudomonas aeruginosa* (NCBI General Identifier Nos. 2498610 and 2498608, respectively) sequences.

TABLE 4

Percent Identity of Amino Acid Sequences Deduced From the
Nucleotide Sequences of cDNA Clones Encoding Polypeptides
Homologous to L-Aspartate Oxidase

| | Percent Identity to | |
|---|---|---|
| SEQ ID NO. | 2498610 | 2498608 |
| 2 | 33.5 | 35.3 |
| 4 | 30.2 | 37.2 |
| 6 | 34.7 | 38.8 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a corn, a soybean and a wheat L-aspartate oxidase. These sequences represent the first plant sequences encoding L-aspartate oxidase.

Example 4

Characterization of cDNA Clones Encoding

Nicotinate-Nucleotide Pyrophosphorylase

The BLASTX search using the EST sequences from clones listed in Table 5 revealed similarity of the polypeptides encoded by the cDNAs to nicotinate-nucleotide pyrophosphorylase from *Arabidopsis thaliana* and *Homo sapiens* (NCBI General Identifier Nos. 4262242 and 2499961, respectively). Shown in Table 5 are the BLAST results for individual ESTs ("EST"):

TABLE 5

BLAST Results for Sequences Encoding Polypeptides Homologous
to Nicotinate-Nucleotide Pyrophosphorylase

| Clone | Status | NCBI General Identifier No. | BLAST pLog Score |
|---|---|---|---|
| tdrlc.pk002.j10 | EST | 4262242 | 23.05 |
| wlm96.pk036.o11 | EST | 2499961 | 23.70 |
| wrl.pk0104.h5 | EST | 4262242 | 73.52 |

The data in Table 6 represents a calculation of the percent identity of the amino acid sequences set forth in SEQ ID NOs:8, 10 and 12 and the *Arabidopsis thaliana* and *Homo sapiens* (NCBI General Identifier Nos. 4262242 and 2499961, respectively) sequences.

TABLE 6

Percent Identity of Amino Acid Sequences Deduced From the
Nucleotide Sequences of cDNA Clones Encoding Polypeptides
Homologous to Nicotinate-Nucleotide Pyrophosphorylase

| | Percent Identity to | |
|---|---|---|
| SEQ ID NO. | 4262242 | 2499961 |
| 8 | 78.8 | 18.2 |
| 10 | 28.4 | 44.0 |
| 12 | 71.6 | 26.4 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a tobacco and two wheat nicotinate-nucleotide pyrophosphorylase. These sequences represent the first tobacco and wheat sequences encoding nicotinate-nucleotide pyrophosphorylase.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 6

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), SmaI, KpnI and XbaI. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 8

Evaluating Compounds for Their Ability to Inhibit the Activity of Quinolinate Metabolic Enzymes The polypeptides described herein may be produced using any number of methods known to those skilled in the art. Such methods include, but are not limited to, expression in bacteria as described in Example 7, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for L-aspartate oxidase are presented by Tedeschi et al. (1987) *Biochemistry* 36:16221–16230. Assays for nicotinate-nucleotide pyrophosphorylase are presented by Iwai and Taguchi (1980) *Methods. Enzymol.* 66:96–101.

What is claimed is:

1. An isolated polynucleotide encoding L-aspartate oxidase having an amino acid sequence set forth in a member selected from the group consisting of SEQ ID NO:2, SEQ ID NO:4, and SEQ ID NO:6.

2. The isolated polynucleotide of claim 1 wherein the polynucleotide is RNA.

3. The isolated polynucleotide of claim 1 wherein the nucleotide sequence of the polynucleotide comprises the sequence set forth in a member selected from the group consisting of SEQ ID NO:1, SEQ ID NO:3, and SEQ ID NO:5.

4. A chimeric gene comprising the polynucleotide of claim 1 operably linked to at least one regulatory sequence.

5. A transformed host cell comprising the chimeric gene of claim 4.

6. An isolated complement of the polynucleotide of claim 1, wherein (a) the complement and the polynucleotide consist of the same number of nucleotides, and (b) the nucleotide sequences of the complement and the polynucleotide have 100% complementarity.

* * * * *

SEQUENCE LISTING

```
<160> NUMBER OF SEQ ID NOS: 12

<210> SEQ ID NO 1
<211> LENGTH: 528
<212> TYPE: DNA
<213> ORGANISM: Zea mays
<220> FEATURE:
<221> NAME/KEY: unsure
<222> LOCATION: (4)
<220> FEATURE:
<221> NAME/KEY: unsure
<222> LOCATION: (18)
<220> FEATURE:
<221> NAME/KEY: unsure
<222> LOCATION: (60)
<220> FEATURE:
<221> NAME/KEY: unsure
<222> LOCATION: (93)
<220> FEATURE:
<221> NAME/KEY: unsure
<222> LOCATION: (163)
<220> FEATURE:
<221> NAME/KEY: unsure
<222> LOCATION: (201)
<220> FEATURE:
<221> NAME/KEY: unsure
<222> LOCATION: (243)
<220> FEATURE:
<221> NAME/KEY: unsure
<222> LOCATION: (296)
<220> FEATURE:
<221> NAME/KEY: unsure
<222> LOCATION: (314)
<220> FEATURE:
<221> NAME/KEY: unsure
<222> LOCATION: (408)

<400> SEQUENCE: 1
acanaaggtc cagagcgngt caaggaacta attgccatgg gtgcctcatt cgaccatggn      60
gaagatggta ggctgcacct tgcaagggaa ggnggtcatt ctcacaacag aattgtccat     120
tctgccgata tgactggaag agagattgaa agagcactgc ttnaagcagt tcacaatgat     180
gataacatat ctttgtttgg ncatcacttt gctattgatc tattgacatg tcagaaaaat     240
ggngaaatct attgctatgg agtggattca atagacattg aaacccagaa ggtagnccgc     300
ttcatctcga aagngacatt gcttgcatca ggaggagctg gccatatata tcccacaacc     360
accaatccac cggtagctac tggggacgga atcgcaatgt gtcatcgngc tcaggctgta     420
```

```
atatccaata tggagtttgt gcagttccat ccaactgcac tttcagatga gggcctgcca    480
ataaagccaa agacaagaag agagaatgca tttctcataa cggaagcg                 528
```

<210> SEQ ID NO 2
<211> LENGTH: 170
<212> TYPE: PRT
<213> ORGANISM: Zea mays
<220> FEATURE:
<221> NAME/KEY: UNSURE
<222> LOCATION: (52)
<220> FEATURE:
<221> NAME/KEY: UNSURE
<222> LOCATION: (96)
<220> FEATURE:
<221> NAME/KEY: UNSURE
<222> LOCATION: (102)

<400> SEQUENCE: 2

```
Pro Glu Arg Val Lys Glu Leu Ile Ala Met Gly Ala Ser Phe Asp His
  1               5                  10                  15

Gly Glu Asp Gly Arg Leu His Leu Ala Arg Glu Gly Gly His Ser His
             20                  25                  30

Asn Arg Ile Val His Ser Ala Asp Met Thr Gly Arg Glu Ile Glu Arg
         35                  40                  45

Ala Leu Leu Xaa Ala Val His Asn Asp Asp Asn Ile Ser Leu Phe Gly
     50                  55                  60

His His Phe Ala Ile Asp Leu Leu Thr Cys Gln Lys Asn Gly Glu Ile
 65                  70                  75                  80

Tyr Cys Tyr Gly Val Asp Ser Ile Asp Ile Glu Thr Gln Lys Val Xaa
                 85                  90                  95

Arg Phe Ile Ser Lys Xaa Thr Leu Leu Ala Ser Gly Gly Ala Gly His
            100                 105                 110

Ile Tyr Pro Thr Thr Thr Asn Pro Pro Val Ala Thr Gly Asp Gly Ile
        115                 120                 125

Ala Met Cys His Arg Ala Gln Ala Val Ile Ser Asn Met Glu Phe Val
    130                 135                 140

Gln Phe His Pro Thr Ala Leu Ser Asp Glu Gly Leu Pro Ile Lys Pro
145                 150                 155                 160

Lys Thr Arg Arg Glu Asn Ala Phe Leu Ile
                165                 170
```

<210> SEQ ID NO 3
<211> LENGTH: 569
<212> TYPE: DNA
<213> ORGANISM: Glycine max

<400> SEQUENCE: 3

```
gcacgaggtg cgctcgacgg ggcggctgaa gcaggccgag tggaggatcg gtgacctgga    60
gtcggagtgg gaggagttcc tgttccggcg ggggtggaag ccgaccacgg tgggcgtcga   120
ggtctgcgag atgcgcaacc tcttctgctg cgccaagctc gtcgtcagga gcgcgctggc   180
caggcgcgag agccgcggcc tgcacttcac cgaggacttc ccgtacctgg aggagagcag   240
gaggaagcct acggtcatct ccccggccgc cgtgcaggag ctcacgtgga gctccaagcc   300
gttgcagagg cagctgcaag cagatgacaa tgcatgcagt tcatccggct gggccttggg   360
gattcgttaa ttcattcatt aatttttaag aactctcagt cgacagcata cacaaaatcc   420
agacagttag gctgtagtag cctgcgtatc tttgcaattc ttgccagttc cagctgttgc   480
```

```
aacttgtaaa cggtgttgtt ggagctgcat tatggtttat gaaccttgat ccgtagtata        540
tgtatgtggt gattggctga ttgcacacc                                          569

<210> SEQ ID NO 4
<211> LENGTH: 86
<212> TYPE: PRT
<213> ORGANISM: Glycine max

<400> SEQUENCE: 4

Val Arg Ser Thr Gly Arg Leu Lys Gln Ala Glu Trp Arg Ile Gly Asp
 1               5                  10                  15

Leu Glu Ser Glu Trp Glu Glu Phe Leu Phe Arg Arg Gly Trp Lys Pro
             20                  25                  30

Thr Thr Val Gly Val Glu Val Cys Glu Met Arg Asn Leu Phe Cys Cys
         35                  40                  45

Ala Lys Leu Val Val Arg Ser Ala Leu Ala Arg Arg Glu Ser Arg Gly
     50                  55                  60

Leu His Phe Thr Glu Asp Phe Pro Tyr Leu Glu Ser Arg Arg Lys
 65                  70                  75                  80

Pro Thr Val Ile Phe Pro
                 85

<210> SEQ ID NO 5
<211> LENGTH: 2065
<212> TYPE: DNA
<213> ORGANISM: Triticum aestivum

<400> SEQUENCE: 5
gcacgaggtt gcagggggctt atctctgcga cgaggagacc gtcaggatag tatgcacaga         60
aggtcctgag cgtgtcaagg agctaatagc catgggtgct tcatttgatc atggtgaaga        120
tggcaggctc caccttgcaa gggaaggtgg acattctcac aacagaatcg tccattctgc        180
cgatatgact ggaaaagaga ttgaaagagc gctgcttcaa gcggttgaaa atgatgagaa        240
catatctgtg ttcggccacc acttcgccat tgatctgttg acctgtcaga ataatggtga        300
aatcttttgt tacggagtgg attcattgga caccaaagct caaaaggtag tccgtttcat        360
ctcaaaagta acattgcttg cgtccggagg agctggccat atatatccca acaaccaa          420 tccaccggtg gctactgggg atggaatcgc aatgtgccat cgcgctcagg ctgtgatatc        480
caatatggag tttgtgcaat tccatccaac tgcactatca gacgaaggcc ttccaataaa        540
gccagctaaa ataagagata atgcatttct tgtaacagaa gcagtcagag agatggagg         600 aattctttac aaccaatcca tggagagatt tatgccttta tacgacgacc gtgccgagtt        660
ggcaccgagg gatgtggttg caagaagcat agatgatcaa ctgaagaaac gtggagagaa        720
gtatgttctc ttggacatca gccacaagcc aagggagaaa attcttgctc attttccgaa        780
cattgcagct gaatgcctgc ggcacggtct ggacatcaca cagcagccca tacctgtcgt        840
ccctgcagct cattacatgt gcggtggtgt tcgggctggg ttgcaagggg agacgagtgt        900
gaaaggcttg tatgtcgctg gtgaggttgc ttgcactgga ttgcacggtg ctaatcgtct        960
tgcaagcaac tcattgctgg aagcgttggt atttgctcag agagccgtgc agccctctat       1020
cgaccacatg gtggatgcgg atgctgaccc ttgtctcgcg gagaaatggg cacgccctgt       1080
gctctctgtc tccattaagg acagtgcact gtctgacatc attgagagga caaagaagac       1140
caggatggag ctgcaatcca taatgtggaa gtacgttggt atagtgcggt cgacgaaccg       1200
gctgaagaat gcagaatgga agattggtga tctagagtca gagtgggagg aattcttatt       1260
```

```
caggaggggc tggaagcctg cctcagtggg gatcgaggcc tgcgaaatga ggaacctctt    1320
ctgctgcgca aagctggttg tgaagagcgc gcttgcgagg cgggagagtc gtggcctgca    1380
cttcactgag gacttcccti acctggagga gagcaagagg aagcctacag tgatcttccc    1440
tactgctatc caagagctaa catggagttc aaagccattg cagaggcagc tgcagtgcaa    1500
atagttgcca cgcccatatc atggagtttt ggggcatgaa gattcattaa tttattaaaa    1560
ttactgaatt aggctgaagt agccttttaa tcttgcagta tactaatcca gcaaagctgg    1620
agttgtaatt gatttttcag ttataattag tctgaagtag cctgttgtat caatgtactt    1680
gcttatttta gcattcacat cagcttcagt gttgtaactt gtcaggtgtg ctggaatca    1740 tgttctgata tttcagatgt ataggacagc agatgatttg tactttattc ctatgctcat    1800
ttaaaaaaaa aaaaaaaaaa aaaaaaaaaa aaaaaaaaa aaaaaaaaaa aaaaaaaaaa    1860
aaaaaaaaaa aaaccccccg ggggggggcc cgggtcccaa attcccccta aagggattcg    1920
tataaccccc gtcaaatggg ccgttttttt aaaaagtctc ggaggggaaa acccggggg    1980 ttacccaatt aattcccctg gaaaaaaacc ccctttccga agtgggtt attacaaaga    2040 gggcccaaac gtttccccttt cccaa                                         2065
```

<210> SEQ ID NO 6
<211> LENGTH: 418
<212> TYPE: PRT
<213> ORGANISM: Triticum aestivum

<400> SEQUENCE: 6

```
Val Ala Gly Ala Tyr Leu Cys Asp Glu Glu Thr Val Arg Ile Val Cys
  1               5                  10                  15

Thr Glu Gly Pro Glu Arg Val Lys Glu Leu Ile Ala Met Gly Ala Ser
             20                  25                  30

Phe Asp His Gly Glu Asp Gly Arg Leu His Leu Ala Arg Glu Gly Gly
         35                  40                  45

His Ser His Asn Arg Ile Val His Ser Ala Asp Met Thr Gly Lys Glu
     50                  55                  60

Ile Glu Arg Ala Leu Leu Gln Ala Val Glu Asn Asp Glu Asn Ile Ser
 65                  70                  75                  80

Val Phe Gly His His Phe Ala Ile Asp Leu Leu Thr Cys Gln Asn Asn
                 85                  90                  95

Gly Glu Ile Phe Cys Tyr Gly Val Asp Ser Leu Asp Thr Lys Ala Gln
            100                 105                 110

Lys Val Val Arg Phe Ile Ser Lys Val Thr Leu Leu Ala Ser Gly Gly
        115                 120                 125

Ala Gly His Ile Tyr Pro Thr Thr Asn Pro Pro Val Ala Thr Gly
        130                 135                 140

Asp Gly Ile Ala Met Cys His Arg Ala Gln Ala Val Ile Ser Asn Met
145                 150                 155                 160

Glu Phe Val Gln Phe His Pro Thr Ala Leu Ser Asp Glu Gly Leu Pro
                165                 170                 175

Ile Lys Pro Ala Lys Ile Arg Asp Asn Ala Phe Leu Val Thr Glu Ala
            180                 185                 190

Val Arg Gly Asp Gly Gly Ile Leu Tyr Asn Gln Ser Met Glu Arg Phe
        195                 200                 205

Met Pro Leu Tyr Asp Asp Arg Ala Glu Leu Ala Pro Arg Asp Val Val
    210                 215                 220
```

```
Ala Arg Ser Ile Asp Asp Gln Leu Lys Lys Arg Gly Glu Lys Tyr Val
225                 230                 235                 240

Leu Leu Asp Ile Ser His Lys Pro Arg Glu Lys Ile Leu Ala His Phe
            245                 250                 255

Pro Asn Ile Ala Ala Glu Cys Leu Arg His Gly Leu Asp Ile Thr Gln
            260                 265                 270

Gln Pro Ile Pro Val Val Pro Ala Ala His Tyr Met Cys Gly Gly Val
        275                 280                 285

Arg Ala Gly Leu Gln Gly Glu Thr Ser Val Lys Gly Leu Tyr Val Ala
    290                 295                 300

Gly Glu Val Ala Cys Thr Gly Leu His Gly Ala Asn Arg Leu Ala Ser
305                 310                 315                 320

Asn Ser Leu Leu Glu Ala Leu Val Phe Ala Gln Arg Ala Val Gln Pro
                325                 330                 335

Ser Ile Asp His Met Val Asp Ala Asp Ala Asp Pro Cys Leu Ala Glu
            340                 345                 350

Lys Trp Ala Arg Pro Val Leu Ser Val Ser Ile Lys Asp Ser Ala Leu
        355                 360                 365

Ser Asp Ile Ile Glu Arg Thr Lys Lys Thr Arg Met Glu Leu Gln Ser
370                 375                 380

Ile Met Trp Lys Tyr Val Gly Ile Val Arg Ser Thr Asn Arg Leu Lys
385                 390                 395                 400

Asn Ala Glu Trp Lys Ile Gly Asp Leu Glu Ser Lys Pro Thr Val Ile
                405                 410                 415

Phe Pro

<210> SEQ ID NO 7
<211> LENGTH: 432
<212> TYPE: DNA
<213> ORGANISM: Nicotiana benthamiana
<220> FEATURE:
<221> NAME/KEY: unsure
<222> LOCATION: (401)
<220> FEATURE:
<221> NAME/KEY: unsure
<222> LOCATION: (409)
<220> FEATURE:
<221> NAME/KEY: unsure
<222> LOCATION: (428)

<400> SEQUENCE: 7
tagtctcgag tttttttttt ttttttttgt tttgttgcag agaaatggag gtgaaagaga      60
gtgagtagaa ggagtgaaag ggaaggagga agaaggaaac gttacccttg aaacagtgca     120
ccagtttgtc caatcttgtg cactgtttca agggtaacat ttcctgaagc ctccgtatca     180
aacctcccat tgatcaattc tacagcctcc ttaagcatcg atacatcaat atctccgtta     240
gataatggaa caaccatatt gtccagcatt atcctaagtc aacgaagtct tgtttgaga      300 tgcatattct aaaacctcac gtacttcttc aattgtcctg gtttcaacct caaccctat      360 ttgaaagctt atttgccccc tccactgtaa cttttgttta nctggatang tgtgatgccc     420
ttgtttgnaa aa                                                         432

<210> SEQ ID NO 8
<211> LENGTH: 66
<212> TYPE: PRT
<213> ORGANISM: Nicotiana benthamiana

<400> SEQUENCE: 8
```

```
Leu Gln Ile Gly Val Glu Val Glu Thr Arg Thr Ile Glu Val Arg
  1               5                  10                  15

Glu Val Leu Glu Tyr Ala Ser Gln Thr Lys Thr Ser Leu Thr Arg Ile
                 20                  25                  30

Met Leu Asp Asn Met Val Val Pro Leu Ser Asn Gly Asp Ile Asp Val
             35                  40                  45

Ser Met Leu Lys Glu Ala Val Gly Leu Ile Asn Gly Arg Phe Asp Thr
 50                  55                  60

Glu Ala
 65
```

<210> SEQ ID NO 9
<211> LENGTH: 430
<212> TYPE: DNA
<213> ORGANISM: Triticum aestivum

<400> SEQUENCE: 9

```
ctcgtgccga attcggcacg agcattttc caggaggtct tcaactacgt tggatgtaaa      60
gtagaatggc tcaaagagga aggctgtggc actcatgata atggcgtaac catagccctc    120
gcaactgtaa cgggaccgct tcgaaaaatt ctccgtggta aagaatcgc ccttaatgtg     180
ttgagccgat gctcttccat tgctacgcag acagataaaa tgattagtat cgcacgaaac    240
gcagggttta aggcagctt ggctggaaca cgcgaaacaa ctcctggctt taggcttgtg     300
gaaaaatacg gctaatcat cggcggcgct gatgctcatc gttttgacct ctcgaatttg    360
acaagtccgt aaaaccccc gaaaaccttg attcctggag tgtaacttgc ttcatgaagc    420
gaattagaga                                                           430
```

<210> SEQ ID NO 10
<211> LENGTH: 116
<212> TYPE: PRT
<213> ORGANISM: Triticum aestivum

<400> SEQUENCE: 10

```
Ser Ala Arg Ala Phe Phe Gln Glu Val Phe Asn Tyr Val Gly Cys Lys
  1               5                  10                  15

Val Glu Trp Leu Lys Glu Glu Gly Cys Gly Thr His Asp Asn Gly Val
                 20                  25                  30

Thr Ile Ala Leu Ala Thr Val Thr Gly Pro Leu Arg Lys Ile Leu Arg
             35                  40                  45

Gly Lys Arg Ile Ala Leu Asn Val Leu Ser Arg Cys Ser Ser Ile Ala
 50                  55                  60

Thr Gln Thr Asp Lys Met Ile Ser Ile Ala Arg Asn Ala Gly Phe Lys
 65                  70                  75                  80

Gly Ser Leu Ala Gly Thr Arg Glu Thr Thr Pro Gly Phe Arg Leu Val
                 85                  90                  95

Glu Lys Tyr Gly Leu Ile Ile Gly Gly Ala Asp Ala His Arg Phe Asp
                100                 105                 110

Leu Ser Asn Leu
            115
```

<210> SEQ ID NO 11
<211> LENGTH: 998
<212> TYPE: DNA
<213> ORGANISM: Triticum aestivum

<400> SEQUENCE: 11

-continued

| | |
|---|---|
| gcacgagcta caatgacgaa ggccatggct gatgctgctc gtcctgcatg catattggaa | 60 |
| acaagaaaaa ctgctccagg tttacgcctg gttgacaagt gggcagtact aattggtggt | 120 |
| gggaagaatc acaggcttgg attatttgat atggttatga taaaagataa tcatatttct | 180 |
| gttgccgggg gcattacaaa tgcaatgaca tctgttgatc agttcttgga aaggaaaat | 240 |
| cttgcagttc ctgttgaggt tgagacaagg acactcgagg aagttagaga tttattgaag | 300 |
| tatactgatg agaacaagac ttcattaact cgtataatgt tggataatat ggtcgtccct | 360 |
| cttccgaatg gggatctaga tgtatcaatg ctcaaagatg cagttcagtt gataaatgga | 420 |
| agatttgaga ccgaggcatc tggaaatgtg acgatggata cggtgaagaa aatcggagaa | 480 |
| actggagtta catacatttc aagtggagcg ttgacgcatt ccgtgaaggc gctcgacata | 540 |
| tctctcaaga tagacaccga gctggctctt caagttggaa ggcgcacaaa tcgtgcctga | 600 |
| caacgcaagc agagtcccac ctgtgtaata acttgacctc ccgttctcct gtacttgtac | 660 |
| aacgcagctc tttgcagcgg acaagatgtt cctctgcctg gcgtggctgg cttgtcggtt | 720 |
| cacattcgac agcaggctcg tcaccgcgct gtgattttc tatctaatat agcaaaggat | 780 |
| gttcggacca acatcacagt tactacagtg tacaatgcaa caacaataat aataagcctg | 840 |
| aatgcccagc ttggaagctg atacaacaaa aggagctctc agtcgttgcc agacatttaa | 900 |
| accgttgact aggcaggtgg aaattgttgc taaatggcgt tgaagaagtt gtatgtgaca | 960 |
| ctacaaaaca cttgtttatc aggaatgggg aacagagc | 998 |

<210> SEQ ID NO 12
<211> LENGTH: 197
<212> TYPE: PRT
<213> ORGANISM: Triticum aestivum

<400> SEQUENCE: 12

```
Ala Thr Met Thr Lys Ala Met Ala Asp Ala Ala Arg Pro Ala Cys Ile
  1               5                  10                  15
Leu Glu Thr Arg Lys Thr Ala Pro Gly Leu Arg Leu Val Asp Lys Trp
             20                  25                  30
Ala Val Leu Ile Gly Gly Gly Lys Asn His Arg Leu Gly Leu Phe Asp
         35                  40                  45
Met Val Met Ile Lys Asp Asn His Ile Ser Val Ala Gly Gly Ile Thr
     50                  55                  60
Asn Ala Met Thr Ser Val Asp Gln Phe Leu Glu Lys Glu Asn Leu Ala
 65                  70                  75                  80
Val Pro Val Glu Val Glu Thr Arg Thr Leu Glu Glu Val Arg Asp Leu
                 85                  90                  95
Leu Lys Tyr Thr Asp Glu Asn Lys Thr Ser Leu Thr Arg Ile Met Leu
            100                 105                 110
Asp Asn Met Val Val Pro Leu Pro Asn Gly Asp Leu Asp Val Ser Met
        115                 120                 125
Leu Lys Asp Ala Val Gln Leu Ile Asn Gly Arg Phe Glu Thr Glu Ala
    130                 135                 140
Ser Gly Asn Val Thr Met Asp Thr Val Lys Lys Ile Gly Glu Thr Gly
145                 150                 155                 160
Val Thr Tyr Ile Ser Ser Gly Ala Leu Thr His Ser Val Lys Ala Leu
                165                 170                 175
```

-continued

```
Asp Ile Ser Leu Lys Ile Asp Thr Glu Leu Ala Leu Gln Val Gly Arg
            180                 185                 190

Arg Thr Asn Arg Ala
            195
```